United States Patent [19]
Kwan et al.

[11] Patent Number: 5,312,760
[45] Date of Patent: May 17, 1994

[54] FRUCTOSAMINE REAGENT AND CALIBRATOR SYSTEM

[75] Inventors: Shing F. Kwan, Ventura; Marjorie Bravo-Leerabhandh, Thousand Oaks, both of Calif.

[73] Assignee: Modrovich, Ivan Endre, Camarillo, Calif.

[21] Appl. No.: 895,606

[22] Filed: Jun. 8, 1992

[51] Int. Cl.⁵ ............................................. G01N 33/74
[52] U.S. Cl. .................................... 436/87; 436/95; 436/166; 436/175; 436/825; 436/904; 514/381
[58] Field of Search ................ 436/87, 88, 95, 175, 436/825, 904, 166; 514/381

[56] References Cited

U.S. PATENT DOCUMENTS

| | | | |
|---|---|---|---|
| 4,642,295 | 2/1987 | Baker | 436/87 |
| 4,645,742 | 2/1987 | Baker | 436/95 X |
| 5,110,745 | 5/1992 | Kricka et al. | 436/87 |
| 5,156,947 | 10/1992 | Siedel et al. | 436/87 X |

*Primary Examiner*—Jill A. Johnston
*Attorney, Agent, or Firm*—Christie, Parker & Hale

[57] ABSTRACT

A system for determining the concentration of fructosamine in sera which consists of a first reagent in which a tetrazolium salt which reduces all reactive substances in sera including fructosamine and a second reagent which is responsive to all reactive substance in sera other than fructosamine. The difference in color change as between the two allows the determination of concentration of fructosamine.

16 Claims, 4 Drawing Sheets

FRUCTOSAMINE REAGENT AND CALIBRATOR SYSTEM

FIELD OF THE INVENTION

Present invention relates to a stable single reagent system for rapid determination of fructosamine concentration in sera.

BACKGROUND OF INVENTION

Fructosamine is an index of the existence of diabetes mellitus in humans. Its measure can be effectively used to reflect patient compliance with treatment, quality of care and efficacy of insulin therapy.

Fructosamine is a product of the interaction of serum glucose with serum proteins, wherein the glucose binds to the amino groups of proteins to form an aldimine, a Schiff base, which undergoes molecular rearrangement to form a stable ketoamine also known as fructosamine. The structure, analysis and clinical usefulness of fructosamine is described by Armbruster in *Clinical Chemistry*, Vol 33. No. 12, pg. 2153-63 (1987) incorporated herein by reference. A method and composition for direct determination fructosamine in blood samples are described in U.S. Pat. Nos. 4,642,295 and 4,645,742 to Baker incorporated herein by reference. The method for determining the level of fructosamine in a blood sample or a sample derived from blood generally involves maintaining the sample at a temperature below 50° C. and at a pH between 10 and 11 and adding a coloring agent (nitro blue tetrazolium or NBT) to the sample. After a first time delay of 10 minutes a first color measurement is taken at a predetermined wavelength of 550 nm and after a second time delay of 2 additional minutes a second color measurement at the predetermined wavelength is taken. The fructosamine level in the sample is determined by comparing the change between the first and second color measurements. This system is employed by Roche and sold as the RoTAG TM plus fructosamine assay. It consists of a buffer (pH 10.3), NBT tablets and a calibrator in solid form. The dye when dissolved is stated to be stable for up to 2 weeks at 2°-8° C. and the calibrator when reconstituted is stated to be stable for up to 4 weeks at 2°-8° C.

A principal shortcoming of the system is a long response time. Conventionally the art desires an assay to be complete in less than 10 minutes and automated analyzers are designated to operate on that cycle. Longer time spans require an undesirable modification to an analysis system and a need exists for an accurate assay which would enable completion within 10 minutes at the normal assay temperature of 37° C.

A separate need is accuracy of the assay. It has been the ongoing quest of the assignee of this invention to develop time stable, single-liquid reagent assay compositions in which each unit is formulated at the source of manufacture and has a shelf life sufficient to remain stable from time of manufacture, storage at the point of manufacture, shipment to any destination in the world and storage at the destination until use. Products to obtain commercially acceptability must have a shelf life of 12 months or more at 2° to 10° C. more typically 18 months at 2° to 10° C., which corresponds to a shelf life of at least about 3 days at 41° C. As indicated, to be commercially adaptive to all spectrophotometric instruments, the compositions must have response time within 10 minutes at 37° C.

It is therefore, the object of this invention to provide a time stable liquid single reagent system for the determination of fructosamine in sera which has a commercially acceptable response time and a stability which is equivalent to at least 12 months at 2° to 10° C.

SUMMARY OF THE INVENTION

The present invention is directed to a novel single reagent system for the rapid determination of fructosamine in sera and procedure therefore.

The novel single reagent system consists of two separate factory formulated reagents preferably supplied with a standard and more preferably with controls for use in the accurate determination of fructosamine in human sera in less than 10 minutes at 37° C.

There is provided a two reagent system for the determination of fructosamine in sera. The first is an alkaline aqueous reagent containing a tetrazolium salt which reacts with all reactive substances in sera including fructosamine an interfering substance to exhibit a measurable first change of color within a predetermined time span of less than about 10 minutes. The second reagent is identical to the first alkaline aqueous reagent, but includes a substance which inhibits reaction of fructosamine with the tetrazolium salt to produce, by reduction of the tetrazolium salt with the reactive substances including interfering substances other than fructosamine, a measurable second change of color in the same predetermined time span as the first reagent. This enables the determination of fructosamine concentration in sera by the difference in the first color change produced using the first alkaline aqueous reagent which reacts with fructosamine and the second color change produced using the second alkaline aqueous reagent. Each color change is produced on the same proportional amount of sera and reagents and after identical predetermined time spans.

The first reagent ("Reagent A" herein) is responsive to all the reactive substances in sera. The second reagent, ("Reagent B" herein), contains a boric acid compound that binds to fructosamine and inhibits the ability of fructosamine to reduce the tetrazolium salt. Reagent B therefore measures all reactive substances except fructosamine that are capable of reducing the tetrazolium salt. The absorbance change obtained with Reagent A less the absorbance change determined with Reagent B gives a net absorbance (Net Delta ABS) which is a measure of fructosamine content of the sera. The concentration of fructosamine in the sample is determined by multiplying the Net Delta ABS by a factor (F) the ratio of fructosamine level of a standard to net absorbance of the standard determined using Reagent A and Reagent B.

Presently preferred composition of Reagent A is about 0.5 mM or 252.85 mg/l p-Iodonitrotetrazolium Violet (INT), 0.1M or 12.4 g/l Sodium Carbonate Monohydrate ($Na_2CO_3$) 0.1M or 8.4 g/l Sodium Bicarbonate ($NaHCO_3$), 0.1M or 6.0 g/l Urea and 1.0% v/v or 10 ml/l Triton X-100 and 1.0% or 10 g/l tergitol NP 40 contained in the deionized water. Solution pH is about 11.0.

Reagent B is identical to Reagent A, but contains 0.12M or 7.416 g/l Boric Acid ($H_3BO_3$) and also has a pH of about 11.0.

The assay protocol is to measure the color change (absorbance) of Reagent A after 2 and 4 or 3 and 5 minutes of reaction and Reagent B at the same 2 and 4 or 3 and 5 minute intervals at a wavelength of about 500 nm at a standard temperature 37° C. The difference in absorbance (ABS) for Reagent A and Reagent B are determined and a difference between the two differentials is then determined. The differential is multiplied by the factor (F) to determine the concentration of fructosamine in micromoles (umol).

In the system, the use of INT in Reagent A enables reduction of INT by fructosamine and all other interfering substance while Reagent B causes reduction of INT by the interfering substances other than fructosamine. By differential therefore, the amount of fructosamine is determined.

This indirect system of determining fructosamine accounts for all of the reactive substances and in so doing effectively eliminates the influence of the reactive substances in a fructosamine determination procedure.

Most significantly, the system enables the use of any absorbance spectrophotometer for the determination of fructosamine in sera since the analysis can be accomplished within in the commercially desired 10 minute time frame.

DETAILED DESCRIPTION

Figure 1:
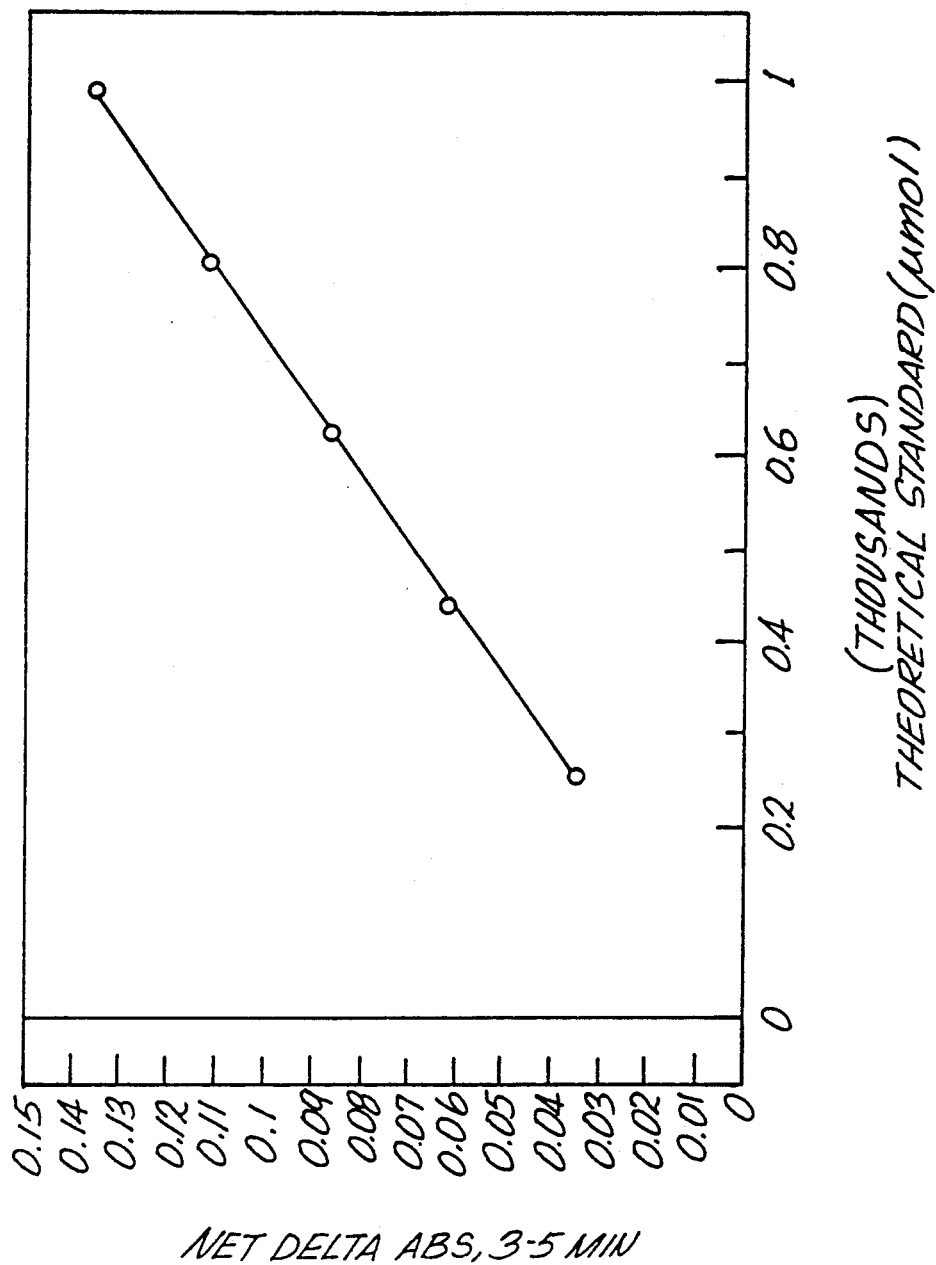
FIG. 1 shows the linearity of the two single reagent fructosamine assay system of the invention.

Present invention is directed to the determination of fructosamine concentration in sera. It is based on the use of one reagent to which is reacted with (reduced by) fructosamine in addition to the most common reactive substances in sera and a second reagent which reacts with the same reactive substances but not fructosamine. By differential therefore, the fructosamine concentration in sera can be determined without the analysis being impacted to any significant degree by the reactive substances. Each reagent contains the same color producing substance preferably p-Iodonitrotetrazolium Violet (INT). The second reagent is identical to the first but contains boric acid which prevents fructosamine from reducing the tetrazolium salt. By the ten reactive substances as used herein there is meant as any substance that may be present in the sample which may be capable of reducing a tetrazolium salt. Such substances include glucose, hemoglobin, bilirubin, ascorbic acid, uric acid, triglycerides, and the like.

Using standard commercial spectrophotometers, the absorbance change for the first reagent minus the absorption change for a second reagent gives a net absorbance change (Net Delta ABS) due to fructosamine. Concentration of fructosamine is then determined by multiplying the net absorbance change by a factor (F) which is derived by dividing the fructosamine concentration of a known standard by the net absorbance change of the standard as determined by measurements taken with Reagent A and Reagent B according to the formula $$F = \frac{\text{Fructosamine Conc. of Standard}}{(\text{Net } ABS \text{ Reagent } A - \text{Net } ABS \text{ Reagent } B)}$$

with fructosamine concentration of the same being determined by the equation:

$$F \times \text{Net Delta ABS (Sample)} = \text{umol fructosamine.}$$

Each composition used in the system is a single liquid reagent. The reagents (Reagent A and B) require no dilution. Quality control is at the point of manufacture. They are aqueous solutions of a carbonate buffer system to maintain reagent pH in the range of about 8.5 to about 11.5 and preferably about 11. Use of other buffer systems such as AMP or CAPS, results in the loss of sensitivity and an increase in average increase in interference.

The tetrazolium salt used in this invention is a compound which will be reduced by fructosamine and interfering substances in the absence of boric acid to a colored formazan product but will only be reduced by the interfering substance other than fructosamine in the presence of boric acid. The preferred tetrazolium salt is p-Iodonitrotetrazolium Violet (INT). Urea is provided in an amount sufficient to minimize interference due to ascorbic acid. Triton X-100 (Octylphenoxy polyethoxy ethanol a non-ionic surfactant having an HLB value of 13.5) solubilizes the products of reduction and increases reagent sensitivity by at least about 30% as compared to a solution without Triton X-100. There may be optionally present another non-ionic surfactant Tergitol NP-40 (an ethoxylated nonylphenol having an HLB value of 17.8) to clarify the sample and minimize interference due to elevated serum triglyceride levels, and which also increases sensitivity. Boric acid is provided to complex with fructosamine and inhibit the reduction of INT by fructosamine. Any other compound which inhibits reduction of INT by fructosamine but not the other reactive substances may be used in place of boric acid.

The carbonate buffer can be used in a concentration of from about 0.01 to about 0.4 M, tetrazolium salt (INT) in a concentration of about 0.1 to 5 mM, urea in a concentration of 0.1 to about 1M, Triton X-100 in a concentration of 0.1 to about 4% by v/v, Tergitol NP-40 in a concentration of about 0 to about 3% v/v of solution.

For the non-fructosamine responsive reagent (Reagent B) boric acid is employed in a concentration of about 0.05 to about 1M. Functional pH range is about 8.5 to about 11.5, preferably 11. At a pH less than about 8.5 sensitivity decreases and the ascorbic acid interference increases. At pH above 11.5 glucose interferes substantially. The fructosamine analytical systems of this invention can be sold as a two component kit with or without a standard which can be separately sold and with or without upper level and lower level controls for calibrating a system which can be sold with the kit or separately. The reagents, standards and control employed in the instant invention have been established to withstand a stress of three days at 47° C. which correlates to a life time of at least 15 to 18 months at 2°-10° C., the normal temperature at which they stored. Being in liquid form there is eliminated the error of reconstituting a lyophilized product and all quality control is exercised at the site of manufacture for uniform performance. More significantly, an assay can be completed in 5 minutes at 37° C. which makes the system adaptive to continuous analyzers which is not the case for the system sold by Roche under the trademark RoTAG. A comparison of the two systems is shown in Table 1 below.

TABLE 1

| Criteria | This Invention | RoTAG |
|---|---|---|
| Reagent Type | Single Liquid | Two part Liquid & Tablet |
| Blank | Yes | No |
| Calibrator | Single Point Liquid | Single Point Lyophilized |
| Controls | Two Levels Liquid | Two Levels Lyophilized |
| Stability | 15 mos. @ 4° C. | Reagent: 2 Wks after reconst. Cal/Control: 4 wks after reconst. |
| Kinetics | Spline Fit | Spline Fit |
| Linearity | 10–1600 umol | To 1000 umol |
| Temperature of Reaction | 37° C. | 37° C. |
| Response Time | <5 Minutes | 10–12 Minutes |
| Specificity | Excellent | Good |
| Precision: 280 umol | | |
| % CV Run to Run | 2.8 | 2.4 |
| With-In Run | 2.9 | 1.9 |
| 500 umol | | |
| Run to Run | 2.8 | 1.7 |
| With-In Run | 2.4 | 2.3 |
| Fructosamine Normal Range | 196–279 umol | 200–272 umol |

The preferred composition Reagent A, which Table 1 is based on, is one containing 0.5 mM p-Iodonitrotetrazolium Violet (INT), 0.1M Sodium Carbonate Monohydrate ($Na_2CO_3$), 0.1M Sodium Bicarbonate ($NaHCO_3$), 0.1M Urea, 1.0 v/v Triton X-100 and 1% Tergitol NP 40 dissolved in deionized water and adjusted to a pH of 11.0. The preferred composition of Reagent B is identical to the Reagent A except that it contains about 0.12 M Boric Acid ($H_3BO_3$) also a pH at 11.0. Reagent A in addition to being reduced by fructosamine will also be reduced by glucose, hemoglobin, bilirubin, ascorbic acid, uric acid and triglycerides within a time frame of 5 minutes or less enabling absorbance color change determinations to be made at time spans of 2 and 4 minutes, preferably 3 and 5 minutes to enable a differential absorbance (Net Delta ABS) for the reduction products to be obtained.

Using Reagent B the same substances are reacted with and produce an absorbance color change in the tetrazolium salt but the reaction does not involve fructosamine which is prevented from reacting with the tetrazolium salt by boric acid.

The preferred assay procedure of the instant invention involves adding to a sample of sera a Reagent A in which INT is reduced by fructosamine and the interfering substances to provide a change in the absorbance as a function of time of, determining the change in absorbance after a given time 2 and 4 or 3 and 5 minute intervals, simultaneously or sequentially reacting another sample of the same sera containing a composition identical to Reagent A but also containing a boric acid which prevents the reduction of the tetrazolium salt with fructosamine, and measuring the absorbance for the same time interval as the first sample. The difference in absorbance for the first sample which is responsive to fructosamine (First Delta ABS) less the difference in absorbance to the second same which is non-responsive to the presence of fructosamine (Second Delta ABS) gives a Net Delta ABS which is multiplied by the Factor (F) to give fructosamine concentration in micromoles (umol). Alternately the micromoles concentration can be determined for each sample with the difference being the fructosamine concentration of the sample.

The fructosamine Assay system of the invention preferably consists of two reagents Reagent A and B which are normally provided with a standard calibrator, normal level control and a high level control. The preparation and use of which are described below.

Preparation of Reagent A

With constant stirring there was sequentially combined at room temperature the following:

| 800 ml | Deionized $H_2O$ |
|---|---|
| 252.85 mg | p-Iodonitrotetrazolium Violet |
| 12.4 g | $Na_2CO_3$ Monohydrate |
| 8.4 g | $NaHCO_3$ |
| 6. g | Urea |
| 10. ml | Triton X-100 |
| 10 g | Tergitol NP 40 |

Solution pH was adjusted to 11.0 with NaOH with constant stirring.

Preparation of Reagent B

With constant stirring at room temperature the following were combined:

| 800 ml | Deionized $H_2O$ |
|---|---|
| 252.85 mg | p-Iodonitrotetrazolium Violet |
| 12.4 g | $Na_2CO_3$ Monohydrate |
| 8.4 g | $NaHCO_3$ |
| 6. g | Urea |
| 10. ml | Triton X-100 |
| 7.416 g | $H_3BO_3$ (Boric Acid) |
| 10 g | Tergitol NP 40 |

As with Reagent A pH was adjusted to 11.0 with NaOH with constant stirring.

Preparation of Calibrator/Control Highly Glycated Fructosamine Intermediate

With constant stirring at room temperature the following were combined:
1. Filtered 50 milliliters of Human Serum through a 0.2 micron cellulose nitrate filter:
2. 0.50 grams Human Albumin Powder Fraction V (Armour Pharmaceutical Co.).
3. 7.20 grams of D-Glucose.
4. 0.01 g $NaN_3$ (Sodium Azide).

Each constituent was added separately with stirring until it went into solution. The solution was sealed in its container with parafilm and incubated for 4 days (96 hours) at 37° C. The solution was dialyzed against 1 liter of deionized water at room temperature for 4 hours, changing the water every hour using a Spectrapor SemiPermeable Membranes, (M.W. Cutoff 12-14,000), where M.W. = molecular weight.

After 4 hours, the water was changed one more time and dialysis continued at 4° C. for an additional 20 hours.

At the end of 20 hours the solution was warmed to room temperature, filtered through a 0.2 micron cellulose nitrate filter (Whatman).

Human Serum Diluent Intermediate

A highly glycated fructosamine intermediate for use in formulating of controls and calibrators was prepared using the procedure described for the Highly Glycated Fructosamine except that using 100 ml of human serum was employed and dialysis was with 2 liters of deionized water.

Working Fructosamine Standard Formulation

The Highly Glycated Fructosamine Intermediate was diluted with the Human Serum Diluent Intermediate in proportion of 1:40 v/v and stabilized by adding 0.5 g of Human Albumin Powder Fraction V, 25 mg of D-glucose and 0.5 ml of Additive AB for each 50 ml of solution. The resultant stabilized standard was filtered through a 0.2 micron cellulose nitrate filter (Whatman). Fructosamine value was in the range of 378–462 umol when assayed.

Normal Level Control Formulation

The Highly Glycated Fructosamine Intermediate was diluted with the Human Serum Diluent Intermediate by adding 2.5 ml of Glycated Fructosamine to 47.5 ml of Diluent. The mixture was stabilized by adding 0.5 g of Human Albumin Powder Fraction V, 25 mg of D-Glucose and 0.5 ml of Additive AB and filtered through a 0.2 micron cellulose nitrate filter (Whatman). Fructosamine value was in the range of 229–281 umol when assayed.

Abnormal High Level Control

The procedure for formulating the normal level control was followed except that 14 ml glycated fructosamine, 36 ml of Dilutent was employed. Fructosamine level was 457–559 umol.

Glycation of Polylysine

With constant stirring at room temperature there was combined:
1. 33 milliliters of 0.1M phosphate buffered saline (pH 7.4).
2. 1.0 grams poly-l-lysine.
3. 4.75 grams of D-glucose.
4. 0.007 grams of $NaN_3$ (sodium azide)

Each was separately dissolved and the container parafilmed and incubated at 37° C. for 4 days (96 hours). After 4 days the solution was dialyzed against 1 liter of deionized water at room temperature for 4 hours, changing the water every hour using Spectrapor Semi-Permeable Membranes, (M. W. Cutoff 12–14,000).

At the end of 20 hours the solution was warmed to room temperature and filtered through a 0.2 micron cellulose nitrate filter (Whatman).

The procedure makes a highly glycated polylysine compound that can be diluted with 0.9% NaCl to obtain a Linearity Set.

Value Assignment Protocol

Using the Roche RoTAG plus as the reference reagent for value assignment, the fructosamine standard, normal and abnormal controls and linearity set were evaluated according to instructions as detailed by Roche at 500 nm.

The instrument employed was Gilford Stasar III using mode ABS at a wavelength of 500 nm and a assay temperature of 37° C. Reagent volume was 1.0 ml, sample volume was 100 ul. The first ABS reading was taken at 3 minutes and a final ABS reading taken at 5 minutes.

The procedure was to allow all reagents and standards to come to room temperature; equilibrate the spectrophotometer to 37° C.; zero the spectrophotometer at 500 nm with deionized water. For each sample 1.0 ml of Reagent A (or Reagent B) was dispensed into a test tube. 100 ul of sample, standard or control was then added to each test tube. The reaction mixture was mixed and immediately aspirated into a flow cell. Absorbance values at 3 minutes and 5 minutes after aspiration were recorded.

The Absorbance (ABS) at 3 minutes and 5 minutes for all tests was determined by the formula:

(5 Min. ABS)−(3 Min. ABS)=Delta ABS (Delta ABS for Reagent A)−(Delta ABS for Reagent B) =Net Delta ABS.

A calculation factor (F) was determined by dividing the concentration of the standard by the Net Delta ABS of the standard.

EXAMPLE:
$$F = \frac{350}{\text{Net Delta } ABS}$$

By multiplying the Net Delta ABS of each sample and control by F determines the Fructosamine concentration of each sample and control according to the formula.

$F \times Net\ Delta\ ABS = umol\ Fructosamine$

The assay system linearity was assayed for linearity using 300 umol calibrator and five levels of human serum pool spiked with various amounts of fructosamine. Table 2 and FIG. 1 summarize the results.

TABLE 2

REAGENT LINEARITY
Assayed on the Cobas Mira
Protocol: 500 nm, 37° C., RV = 200 ul, SV = 20 ul
Absorbance Measured at 3 and 5 minutes

| Sample | Actual Delta ABS | Net [umol] | Actual [umol] | Theoretical |
|---|---|---|---|---|
| 300 Std | .0410 | 300 | — | Mix of 1 & 5 |
| 1 | .0348 | 255 | 255 | 1 |
| 2 | .0614 | 449 | 439 | [(3 × 1) + 5]/4 |
| 3 | .0863 | 632 | 623 | (1 + 5)/2 |
| 4 | .1115 | 816 | 806 | [1 + (3 × 5)]/5 |
| 5 | .1353 | 990 | 990 | 5 |

Linearity/Dynamic Range

Protein glycation occurs at the epsilon amino groups of lysines. To achieve a fructosamine level to challenge linearity glucose was incubated with polylysine. Each lysine residue is a potential site of glycation. This concentrated glycated polylysine was diluted in 0.9% NaCl to obtain six levels of glycated polylysine as reported in Table 3.

TABLE 3

Glycated Polylysine Dilution Protocol

| Factor | Dilution Level = | Dilution with NaCl |
|---|---|---|
| 1 | 1X Glyc. Poly. + 19X NaCl | .05 |
| 2 | 1x Glyc. Poly. + 9X NaCl | .10 |
| 3 | 1X Glyc. Poly. + 3X NaCl | .25 |
| 4 | 1X Glyc. Poly. + 1X Nacl | .50 |
| 5 | 1X Glyc. Poly + 1X NaCl | .75 |
| 6 | Undiluted Glyc. Poly. (Neat) | 1.00 |

Figure 2:
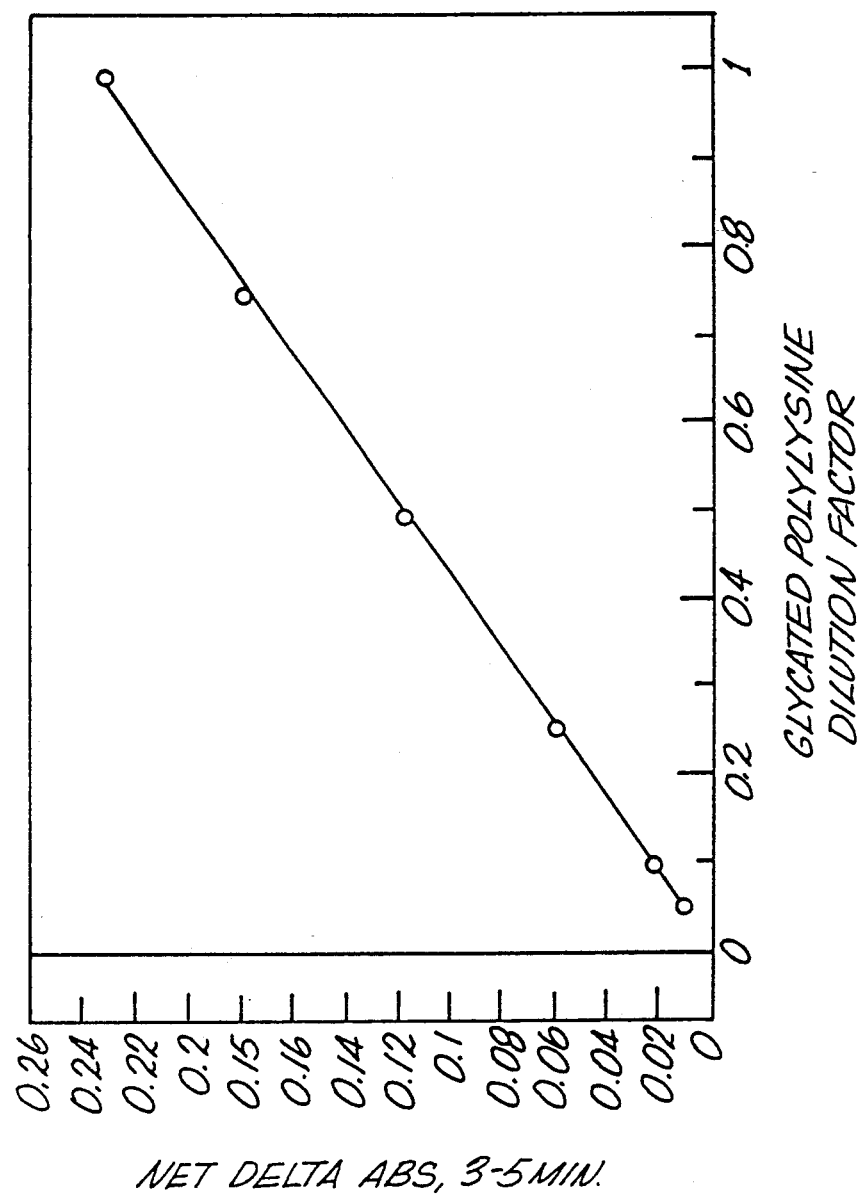
FIG. 2 illustrates retention of linearity for diluted sera.

Table 4 and FIG. 2 summarize the linearity results which establishes that the system is functional for diluted area.

TABLE 4

LINEARITY/DYNAMIC RANGE
Assayed on the Cobas Mira
MAS protocol: 500 nm, 37° C., RV = 200 ul, SV = 20 ul
Absorbance Measured at 3 and 5 Minutes

| Sample | Dilution Factor | Net Delta ABS | Umol Fructosamine |
|---|---|---|---|
| 300 Std | / | .0399 | 300 |
| 1 | .05 | .0093 | 70 |
| 2 | .10 | .0217 | 163 |
| 3 | .25 | .0590 | 444 |
| 4 | .50 | .1163 | 874 |
| 5 | .75 | .1784 | 1341 |
| 6 | 1.00 | .2310 | 1737 |

Precision

Biocell Blood Bank Segments Pool was spiked with glycated human serum to levels of 280 umol and 500 umol fructosamine for use in precision (Run to run) and within-run studies. Table 4 lists the results of Run to Run Performance.

TABLE 4

RUN TO RUN PERFORMANCE
Assayed on the Cobas Mira
Protocol: 500 nm, 37° C., RV = 200 ul, SV = 20 ul
Absorbance Measured at 3 and 5 Minutes
Standard: In-House 300 umol
Based on Single Calibration Day 1
Daily Value is Average of Triplicate Analyses

| Day | 280 umol | 500 umol |
|---|---|---|
| 1 | 272 | 492 |
| 2 | 277 | 513 |
| 3 | 288 | 505 |
| 4 | 284 | 478 |
| 5 | 270 | 488 |
| N | 5 | 5 |
| Minimum | 270 | 478 |
| Maximum | 288 | 513 |
| Mean | 278 | 495 |
| Std Dev | 7.7 | 13.9 |
| % CV | 2.8 | 2.3 |

The results are excellent for a two reagent system. It also appears that the system can hold a calibration for at least 5 days.

Within Run performance was also evaluated with the same two samples. Table 5 summarizes the results.

TABLE 5

WITH-IN RUN REFERENCE
Assayed on the Cobas Mira
Protocol: 500 nm, 37° C., RV = 200 ul, SV = 20 ul
Reaction Measured from at 3 and 5 minutes
Standard: 300 umol

| Sample | Repetitions | | | | |
|---|---|---|---|---|---|
| 280 umol | 294 | 293 | 289 | 297 | 285 |
| | 282 | 277 | 272 | 291 | 272 |
| | 292 | 276 | 285 | 304 | 289 |
| | 294 | 290 | 290 | 288 | 281 |
| 500 umol | 501 | 491 | 494 | 504 | 514 |
| | 511 | 497 | 504 | 515 | 523 |
| | 495 | 494 | 503 | 507 | 510 |
| | 511 | 475 | 515 | 525 | 498 |

| | 280 umol | 500 umol |
|---|---|---|
| N | 20 | 20 |
| Minimum | 272 | 475 |
| Maximum | 304 | 525 |
| Mean | 287 | 504 |
| Std Dev | 8.4 | 11.9 |

TABLE 5-continued

WITH-IN RUN REFERENCE
Assayed on the Cobas Mira
Protocol: 500 nm, 37° C., RV = 200 ul, SV = 20 ul
Reaction Measured from at 3 and 5 minutes
Standard: 300 umol

| % CV | 2.9 | 2.4 |
|---|---|---|

The With-In Run precision is excellent.

Correlation

For correlation study 122 samples were assayed.
85 Normal Patients from Biocell Blood Bank Segment
18 Diabetic Patients
10 Randomly Glycated samples from LRRMC
9 Related Levels of Glycated Biocell Pool Each sample was assayed in triplicate. Each sample was assayed with fructosamine assay kept at 4° C. and Roche RoTAG Plus. The results are tabulated and presented in Table 6.

TABLE 6

PATIENT SAMPLE CORRELATION FRUCTOSAMINE SYSTEM (FS) vs ROCHE
Assayed on the Cobas Mira 37° C.
FS: RV = 200 ul, SV = 20 ul
Wavelength 500 nm
Standard: 300 umol
Absorbance Measured at 3 and 5 minutes
ROCHE: RV = 200 ul, Dil. Vol. = 30 ul, SV = 10 ul
Wavelength 550 nm
Standard: Roche 442 umol
Absorbance Measured at 10 and 12 minutes

| | Roche umol | FS umol |
|---|---|---|
| Normal Samples | | |
| 1 | 195 | 176 |
| 2 | 188 | 184 |
| 3 | 216 | 245 |
| 4 | 165 | 149 |
| 5 | 220 | 178 |
| 6 | 216 | 239 |
| 7 | 219 | 209 |
| 8 | 234 | 265 |
| 9 | 215 | 245 |
| 10 | 232 | 241 |
| 11 | 224 | 234 |
| 12 | 231 | 232 |
| 13 | 240 | 250 |
| 14 | 174 | 165 |
| 15 | 240 | 247 |
| 16 | 240 | 197 |
| 17 | 229 | 206 |
| 18 | 202 | 193 |
| 19 | 206 | 202 |
| 20 | 222 | 190 |
| 21 | 282 | 263 |
| 22 | 262 | 246 |
| 23 | 251 | 215 |
| 24 | 252 | 214 |
| 25 | 245 | 194 |
| 26 | 276 | 220 |
| 27 | 196 | 198 |
| 28 | 238 | 218 |
| 29 | 253 | 259 |
| 30 | 212 | 231 |
| 31 | 219 | 211 |
| 32 | 219 | 226 |
| 33 | 235 | 237 |
| 34 | 192 | 201 |
| 35 | 210 | 230 |
| 36 | 212 | 221 |
| 37 | 240 | 229 |
| 38 | 253 | 253 |
| 39 | 244 | 266 |
| 40 | 242 | 244 |
| 41 | 171 | 180 |
| 42 | 233 | 250 |

TABLE 6-continued

PATIENT SAMPLE CORRELATION FRUCTOSAMINE SYSTEM (FS) vs ROCHE
Assayed on the Cobas Mira 37° C.
FS: RV = 200 ul, SV = 20 ul
Wavelength 500 nm
Standard: 300 umol
Absorbance Measured at 3 and 5 minutes
ROCHE: RV = 200 ul, Dil. Vol. = 30 ul, SV = 10 ul
Wavelength 550 nm
Standard: Roche 442 umol
Absorbance Measured at 10 and 12 minutes

|  | Roche umol | FS umol |
|---|---|---|
| 43 | 228 | 239 |
| 44 | 196 | 250 |
| 45 | 208 | 242 |
| 46 | 202 | 220 |
| 47 | 209 | 209 |
| 48 | 252 | 258 |
| 49 | 245 | 227 |
| 50 | 191 | 203 |
| 51 | 222 | 241 |
| 52 | 246 | 240 |
| 53 | 473 | 495 |
| 54 | 214 | 217 |
| 55 | 225 | 233 |
| 56 | 226 | 211 |
| 57 | 244 | 226 |
| 58 | 243 | 263 |
| 59 | 226 | 260 |
| 60 | 208 | 229 |
| 61 | 243 | 236 |
| 62 | 200 | 197 |
| 63 | 171 | 168 |
| 64 | 215 | 214 |
| 65 | 284 | 215 |
| 66 | 248 | 275 |
| 67 | 269 | 289 |
| 68 | 203 | 204 |
| 69 | 234 | 234 |
| 70 | 222 | 223 |
| 71 | 209 | 242 |
| 72 | 227 | 219 |
| 73 | 203 | 215 |
| 74 | 227 | 245 |
| 75 | 225 | 238 |
| 76 | 209 | 202 |
| 77 | 229 | 206 |
| 78 | 224 | 216 |
| 79 | 230 | 255 |
| 80 | 247 | 203 |
| 81 | 189 | 152 |
| 82 | 251 | 198 |
| 83 | 344 | 357 |
| 84 | 171 | 174 |
| 85 | 616 | 671 |
| Diabetic Samples | | |
| 86 | 375 | 365 |
| 87 | 295 | 278 |
| 88 | 374 | 379 |
| 89 | 254 | 250 |
| 90 | 397 | 450 |
| 91 | 291 | 277 |
| 92 | 377 | 383 |
| 93 | 377 | 383 |
| 94 | 367 | 359 |
| 95 | 250 | 243 |
| 96 | 395 | 432 |
| 97 | 283 | 278 |
| 98 | 378 | 400 |
| 99 | 282 | 283 |
| 100 | 376 | 390 |
| 101 | 244 | 238 |
| 102 | 386 | 447 |
| 103 | 278 | 266 |
| Glyc. LRRMC | | |
| 104 | 291 | 256 |
| 105 | 473 | 477 |
| 106 | 310 | 343 |
| 107 | 327 | 360 |
| 108 | 451 | 476 |
| 109 | 513 | 541 |
| 110 | 371 | 335 |
| 111 | 489 | 485 |
| 112 | 286 | 266 |
| 113 | 345 | 342 |
| Glyc. Biocell | | |
| 114 | 286 | 262 |
| 115 | 403 | 389 |
| 116 | 534 | 517 |
| 117 | 668 | 673 |
| 118 | 799 | 835 |
| 119 | 917 | 938 |
| 120 | 1102 | 1100 |
| 121 | 1180 | 1196 |
| 122 | 1304 | 1357 |
| N | 122 | 122 |
| Minimum | 165 | 149 |
| Maximum | 1304 | 1357 |
| Mean | 301 | 302 |
| Std Dev | 185 | 192 |
| Linear Regression | Slope = | 1.032883 |
|  | Std Err = | 0.011610 |
|  | Y-Intercept = | −8.67445 |
|  | Std Err = | 23.57628 |
|  | Corr. Coef. | 0.992503 |

Figure 3:
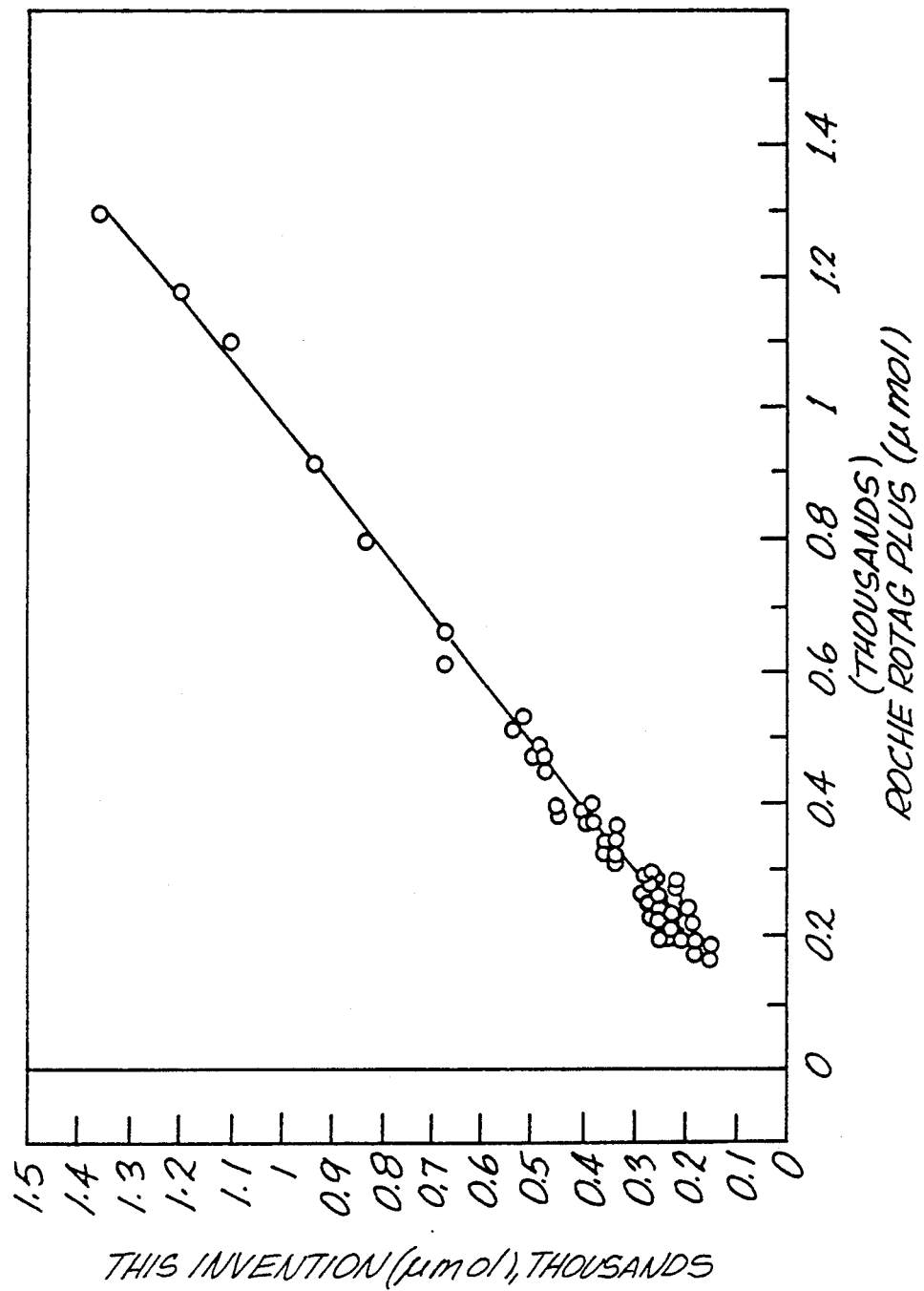
FIGS. 3 and 4 correlate the performance of the Fructosamine Assay System of the invention against RoTAG plus a manufacture and sold by Roche.
Figure 4:
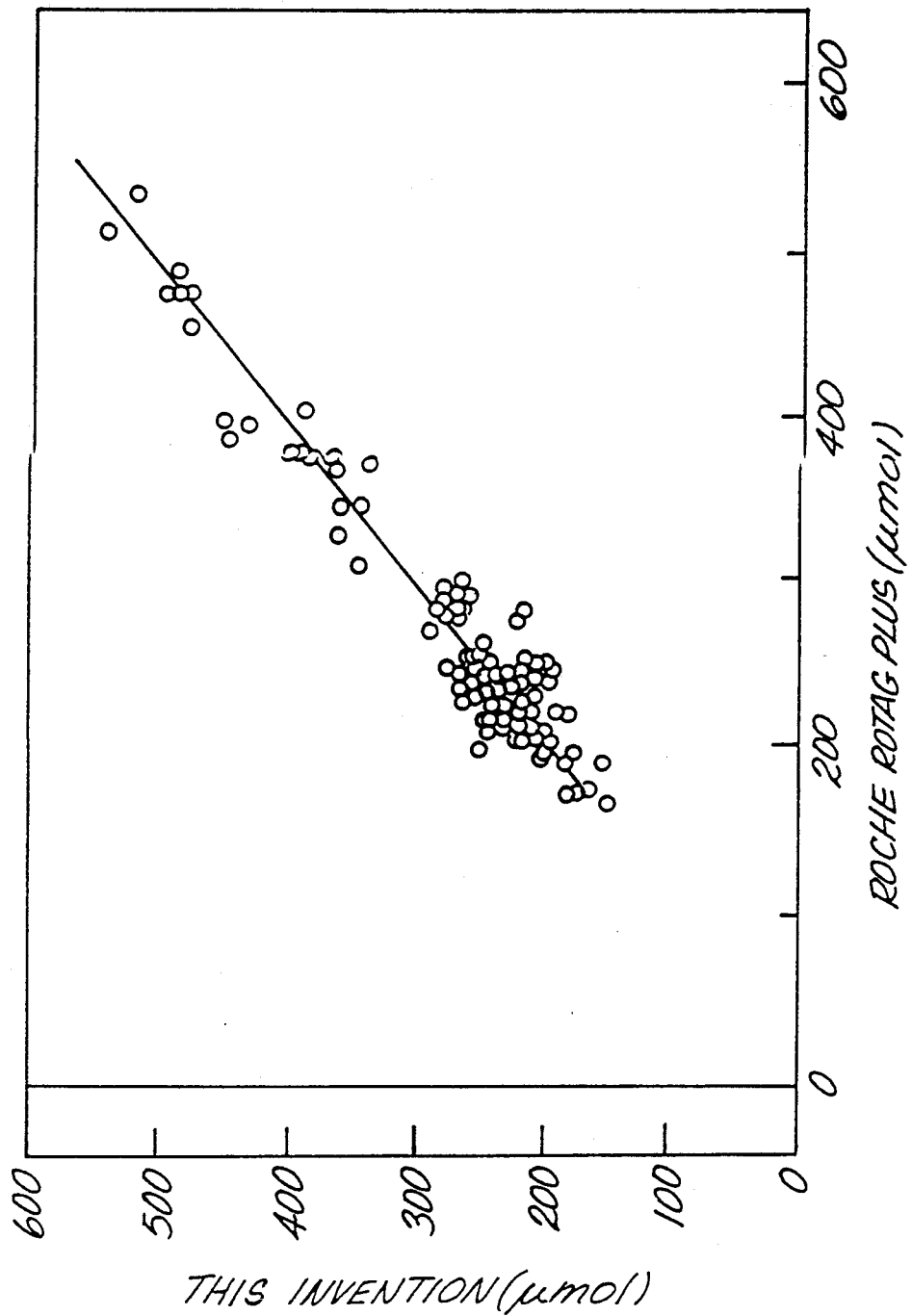

FIGS. 3 and 4 illustrate the results of the correlation between fructosamine system of this invention 4° C. and Roche RoTAG plus and establishes that excellent correlation of the two systems where the system of this invention is substantially faster recovery.

Stress Test

Reagents A and B and the standard were stressed at 4° C. and 47° C. for 3 days. Each of the reagents were then evaluated for Ai, endogenous rate and the reagent kit for recovery of 20 patient samples. Table 7 lists the results of the Ai analysis and endogenous rate.

TABLE 7

FRUCTOSAMINE STRESS STUDY - Ai AND ENDOGENOUS RATE
Reagent A and B stresses 3 days at 4° C. and 47° C. assayed
on the Gilford Stasar III - 500 nm, 37° C. Reaction measured at 0 and 5 minutes

| Reagent/Temperature | ABS, 0 Min | ABS, 5 Min |
|---|---|---|
| Reagent A 4° C. | .060 | .062 |
| Reagent A 47° C. | .373 | .375 |
| Reagent B 4° C. | .068 | .069 |
| Reagent B 47° C. | .383 | .384 |

The Ai increases upon stress, but remains acceptable. The endogenous rate from 0–5 Minutes is less than 0.002 and is negligible.

Table 8 shows the results of assaying the stresses reagents with the stressed standard and the 20 patient samples.

TABLE 8

FRUCTOSAMINE STRESS STUDY
Reagent A and B Stressed 3 days at 4° C. and 47° C.
Standard; 320 umol stressed 3 days at 4° C. and 47° C.
Assayed on the Cobas Mira 500 nm, 37° C. Reagent
Volume 200 ul, Sample Volume 20 ul absorbance
measured at 3 and 5 minutes

| Patient Sample | 4° C. umol | 47° C. umol | 47° C. % Rec |
|---|---|---|---|
| 1 | 202 | 239 | 118 |
| 2 | 238 | 247 | 104 |
| 3 | 222 | 225 | 101 |
| 4 | 240 | 242 | 101 |
| 5 | 223 | 229 | 103 |
| 6 | 185 | 194 | 105 |
| 7 | 180 | 204 | 113 |
| 8 | 292 | 254 | 87 |
| 9 | 170 | 192 | 113 |
| 10 | 650 | 616 | 95 |
| 11 | 282 | 280 | 99 |
| 12 | 501 | 462 | 92 |
| 13 | 331 | 325 | 93 |
| 14 | 366 | 371 | 101 |
| 15 | 487 | 471 | 97 |
| 16 | 555 | 537 | 97 |
| 17 | 365 | 368 | 101 |
| 18 | 486 | 483 | 99 |
| 19 | 274 | 291 | 106 |
| 20 | 359 | 366 | 102 |

In a couple of instances the 47° C. stressed over-recovers, but in most cases the recoveries are very good. Percent recoveries range between 87 and 118 percent. The stability is acceptable after 3 days at 47° C.

What is claimed is:

1. A reagent system for the determination of fructosamine in sera which comprises:
   (a) a first alkaline aqueous reagent containing a tetrazolium salt which reacts with all reactive substances in sera including fructosamine and interfering substances to exhibit a measurable first change of color within a predetermined time span of less than about 10 minutes in consequence of the reaction of the tetrazolium salt with fructosamine and the interfering substances; and
   (b) a second reagent identical to the first alkaline aqueous reagent and boric acid in an amount sufficient to inhibit reaction of fructosamine with the tetrazolium salt to produce by reduction of the tetrazolium salt with the reactive substances including interfering substances other than fructosamine a measurable second change of color in the same predetermined time span as the first reagent to enable the determination of fructosamine concentration in sera by the difference in the first color change produced using the first alkaline aqueous reagent which reacts with fructosamine and the second color change produced using the second alkaline aqueous reagent each color change produced on the same proportional amount of sera and after identical predetermined time spans.

2. The reagent system as claimed in claim 1 in combination with a liquid standard containing a predetermined amount of fructosamine which when used with said first and second alkaline aqueous reagents enable the determination of a factor used as multiplier used to compute from the difference in color change the fructosamine concentration in a sera sample.

3. An assay system as claimed in claim 2 further including a liquid normal level fructosamine control and a liquid high level fructosamine control.

4. An assay system as claimed in claim 3 further including a liquid normal fructosamine level control having a fructosamine range of 229–281 $\mu$mol, when assayed, and a liquid high fructosamine level control having a fructosamine range, when assayed, of 457–559 $\mu$mol.

5. An assay system as claimed in claim 2 further including a liquid normal level fructosamine control having a fructosamine range of 229–281 $\mu$mol, when assayed, and a liquid high fructosamine level control having a fructosamine range, when assayed, of 457–559 $\mu$mol.

6. A reagent system for the determined of fructosamine in sera at 37° C. which comprises:
   (a) a first liquid reagent which is an aqueous solution of a carbonate buffer present in a concentration from about 0.1 to about 0.4 molar, a tetrazolium salt which is reduced by fructosamine and interfering substances in sera present in a concentration of about 0.1 to about 5 millimolar urea in a concentration of about 0.1 to about 1 molar, octylphenoxy polyethoxyethanol in a concentration of about 0.1 to about 4% volume by volume, and from 0 to 3% v/v ethoxylated nonylphenol, said solution having a pH of from about 8.5 to about 11.5; and
   (b) a second liquid reagent identical to the first reagent and further containing boric acid in a concentration of about 0.05 to about 1 molar, said first reagent producing a first color within a predetermined time span of less than 10 minutes and said second reagent producing a second color during the same time span to enable by color difference a determination of fructosamine in sera.

7. A reagent system as claimed in claim 6 in which the tetrazolium salt is p-Iodonitrotetrazolium Violet.

8. A reagent system as claimed in claim 7 in combination with a standard containing a known amount of fructosamine which when used with said first and second liquid alkaline aqueous reagents to determine a factor used as a multiplier to determine from the difference in color change fructosamine concentration in a sera sample.

9. A reagent system as claimed in claim 6 in combination with a standard containing a known amount of fructosamine which when used with said first and second liquid alkaline aqueous reagents to determine a factor used as a multiplier to determine from the difference in color change fructosamine concentration in a sera sample.

10. A reagent system for the determination of fructosamine in sera which comprises:
   (a) a first liquid reagent containing 0.5 millimolar p-Iodonitrotetrazolium Violet, about 0.1 molar sodium carbonate monohydrate, about 0.1 molar sodium bicarbonate, about 0.1 molar urea, about 1% volume by volume of octylphenoxy polyethoxyethanol, and 1% volume by volume ethoxylated nonylphenol dissolved in the deionized water and having a pH of about 11; and
   (b) a second liquid reagent identical to the first reagent but further including about 0.12 molar boric acid and also having a pH of about 11, said reagent system being stable for at least 1 year at 2°–10° C. and cooperating with the first liquid reagent to enable completion of a fructosamine assay determined by a difference in color change using the first liquid reagent and the second liquid reagent in the same proportional amount of sera during identical periods of time, both within 10 minutes at 37° C.

11. A reagent system as claimed in claim 7 in combination with a liquid standard containing a predetermined amount of fructosamine which when used with said first and second liquid alkaline aqueous reagents enable the determination a factor used as a multiplier used to compute from the difference in color change produced by the first and second liquid reagents the fructosamine concentration in a sera sample.

12. A reagent system as claimed in claim 11 in which the standard provides a fructosamine value in the range of about 300 to 500 μmol.

13. A method for determining fructosamine in sera which comprises:
  (a) determining a first absorbance of a first color produced by reaction of a first liquid reagent containing a tetrazolium salt with a first amount of sera, said first color produced in consequence of reduction by fructosamine and other interfering substances in said sera of said tetrazolium salt, said first absorbance determined at two predetermined points in time, each within 10 minutes at 37° C.;
  (b) determining a second absorbance of a second color produced by reaction of a second liquid reagent in an amount equal to the amount of said first liquid reagent with sera in an amount equal to said first amount of said sera using a second liquid reagent containing a tetrazolium salt and boric acid which produces a second color change by reaction of the tetrazolium salt with interfering substances in the sera other than fructosamine, said boric acid being in an amount sufficient to inhibit the reaction of fructosamine with the tetrazolium salt, said second absorbance being determined at two predetermined points in time, each within 10 minutes at 37° C.; and
  (c) determining the fructosamine concentration in said sera as a function of the difference in the first and second color change produced using the first liquid reagent which reacts with fructosamine and the second liquid reagent which is inhibited from reacting with fructosamine.

14. A method of determining the concentrate of fructosamine in sera at 37° C. which comprises:
  (a) adding to a first sample of sera a first liquid reagent which reacts with fructosamine and interfering substances and is an aqueous solution of a carbonate buffer present in a concentration of from about 0.1 to about 0.4 molar, a tetrazolium salt which is reduced by fructosamine and interfering substances in sera present in a concentration of about 0.1 to about 1 molar of a 100% by volume octylphenoxy polyethoxyethanol in a concentration of about 0.1 to about 4% v/v and from 0 to 3% v/v ethoxylated nonylphenol, said solution having a pH of from about 8.5 to about 11.5 and measuring the change in absorbance of the sera added reagent at 500 nm at 2 or 3 minutes of the addition of the reagent and at 2 minutes after the first measurement of absorbance;
  (b) repeating the procedure of step (a) using a second sample of the sera of the same volume as the first sample of sera by addition of a second liquid reagent identical in volume and content of the first reagent and further containing boric acid in a concentration of about 0.05 to about 1 molar to inhibit reaction with fructosamine; and
  (c) determining from the difference in change of absorbance in step (a) and the change of absorbance in step (b) the fructosamine concentration in the sera.

15. A method as claimed in claim 14 in which the tetrazolium salt is p-Iodonitrotetrazolium violet.

16. A method of determining the concentrate of fructosamine in sera which comprises:
  (a) adding to a predetermined amount of sera a first liquid reagent containing 0.5 millimolar p-Iodonitrotetrazolium Violet, about 0.1 molar sodium carbonate monohydrate, about 0.1 molar sodium bicarbonate, about 0.1 molar urea, about 1% v/v octylphenoxy polyethoxyethanol, and 1% w/v ethoxylated nonylphenol dissolved in the deionized water and having a pH of about 11 and determining absorbance at 37° C. of 500 nm 2 and 4 minutes or 3 and 5 minutes after addition of the first liquid reagent to the sera;
  (b) repeating step (a) by adding to another sample of the sera, of same proportional amount as the first, a second liquid reagent identical in proportional volume and content of the first reagent but further containing about 0.12 molar boric acid and having a pH of about 11; and
  (c) using the difference in absorbance determined in step (a) and the differential in absorbance determined in step (b) to determine the fructosamine content of the sera.

* * * * *

UNITED STATES PATENT AND TRADEMARK OFFICE
CERTIFICATE OF CORRECTION

PATENT NO. : 5,312,760

DATED : May 17, 1994

INVENTOR(S) : Shing F. Kwan; Marjorie Bravo-Leerabhandh

It is certified that error appears in the above-indentified patent and that said Letters Patent is hereby corrected as shown below:

On title page:

Abstract, line 5, change "substance" to -- substances --.

Column 1, line 6, change "Present invention" to -- The present invention --.
Column 1, line 10, before "INVENTION" insert -- THE --.
Column 1, line 64, change "commercially" to -- commercial --.
Column 3, line 8, change "(umol)" to -- ($\mu$mol) --.
Column 3, line 22, after "within" delete "in".
Column 3, line 27, after "assay" change "system" to -- systems --.
Column 3, line 35, change "Present Invention" to -- The present invention --.
Column 3, line 49, after "meant" delete "as".
Column 4, line 4, change "umol" to -- $\mu$mol --.
Column 4, line 61, before "stored" insert -- are --.
Column 5, line 22, change "500 umol" to -- 500 $\mu$mol --.
Column 5, line 25, change "196-279 umol" to -- 196-279 $\mu$mol --; and change "200-272 umol" to -- 200-272 $\mu$mol --.
Column 6, line 31, change "NaHCo$_3$" to -- NaHCO$_3$ --.
Column 7, line 13, change "umol" to -- $\mu$mol --.
Column 7, line 24, change "umol" to -- $\mu$mol --.
Column 7, line 30, change "Dilutent" to -- Diluent --.
Column 7, line 31, change "umol" to -- $\mu$mol --.

UNITED STATES PATENT AND TRADEMARK OFFICE
CERTIFICATE OF CORRECTION

PATENT NO. : 5,312,760
DATED : May 17, 1994
INVENTOR(S) : Shing F. Kwan; Marjorie Bravo-Leerabhandh It is certified that error appears in the above-indentified patent and that said Letters Patent is hereby corrected as shown below:

Column 7, line 61, before "assay" change "a" to -- an --.
Column 7, line 63, change "100 ul" to -- 100 $\mu$l --.
Column 8, line 2, change "ul" to -- $\mu$l --.
Column 8, line 38, change "ul" to -- $\mu$l -- (both occurrences).
Column 9, lines 4,26, there are two tables numbered "TABLE 4."  Change "TABLE 4" Page 17(second occurrence) to -- TABLE 4A --.
Column 9, lines 2,3, cange "diluted area" to -- diluted sera --.
Column 9, line 7, change "ul" to -- $\mu$l -- (both occurrences).
Column 9, line 10, change "Umol" to -- Mmol --.
Column 9, lines 21,22, change "umol" to -- $\mu$mol -- (both occurrences).
Column 9, line 29, change "ul" to -- $\mu$l -- (both occurrences).
Column 9, lines 31, 34, change "umol" to -- $\mu$mol -- (all occurrences).
Column 9, line 53, change "ul" to -- $\mu$l -- (both occurrences).
Column 9, lines 55,57,61,64, in TABLE 5 change "umol" to -- $\mu$mol -- (all occurrences).
Column 10, line 4, in TABLE 5-continued change "ul" to -- $\mu$l -- (both occurrences).
Column 10, line 6, in TABLE 5-continued change "umol" to -- $\mu$mol --.
Column 10, lines 26, 29, in TABLE 6 change "ul" to -- $\mu$l -- (all occurrences).

UNITED STATES PATENT AND TRADEMARK OFFICE
CERTIFICATE OF CORRECTION

PATENT NO. : 5,312,760

DATED : May 17, 1994

INVENTOR(S) : Shing F. Kwan; Marjorie Bravo-Leerabhandh

It is certified that error appears in the above-indentified patent and that said Letters Patent is hereby corrected as shown below:

Column 10, lines 27,30,34, in TABLE 6 change "umol" to -- μmol -- (all occurrences).
Column 11, lines 5,9, in TABLE 6-continued change "ul" to -- μl -- (all occurrences).
Column 11, lines 7,10,12, in TABLE 6-continued change "umol" to -- μmol -- (all occurrences).
Column 12, lines 5,9, in TABLE 6-continued change "ul" to -- μl -- (all occurrences).
Column 12, lines 7,10,12, in TABLE 6-continued change "umol" to -- μmol -- (all occurrences).
Column 12, line 39, after "establishes" delete "that".
Column 12, line 41, after "substantially" insert -- a --.
Column 12, line 65, after "stresses" insert -- of the --.
Column 13, lines 4,9, in TABLE 8 change "umol" to -- μmol -- (all occurrences).
Column 13, line 6, in TABLE 8 Change "ul" to -- μl -- (both occurrences).

In the Claims:

Column 13, line 63, after "multiplier" delete "used".
Column 14, line 13, change "determined" to -- determination --.

Column 15, line 3, change "claim 7" to -- claim 10 --.
Column 15, line 8, before "to compute" delete "used".

UNITED STATES PATENT AND TRADEMARK OFFICE
CERTIFICATE OF CORRECTION

PATENT NO. : 5,312,760

DATED : May 17, 1994

INVENTOR(S) : Shing F. Kwan; Marjorie Bravo-Leerabhandh

It is certified that error appears in the above-indentified patent and that said Letters Patent is hereby corrected as shown below:

Column 15, line 22, after "determined at" insert -- a first --.
Column 15, line 26, after "amount" (1st occurrence) insert -- proportionally --.
Column 15, line 27, after "amount" insert -- proportionately --.
Column 15, line 35, after "determined at" insert -- a second --.
Column 15, line 37, after "C." insert -- and in an amount proportionately equal to the first two predetermined points in time --.
Column 16, line 33, change "1% w/v" to -- 1% v/v --.
Column 16, line 40, after "of" insert -- the --.

Signed and Sealed this

Twenty-fifth Day of April, 1995

Attest:

BRUCE LEHMAN

Attesting Officer     Commissioner of Patents and Trademarks